(12) United States Patent
Zare et al.

(10) Patent No.: US 11,416,704 B2
(45) Date of Patent: Aug. 16, 2022

(54) GROUP CLASSIFICATION BASED ON MACHINE LEARNING ANALYSIS OF MASS SPECTROMETRY DATA FROM SWEAT

(71) Applicant: The Board of Trustees of the Leland Stanford Junior University, Palo Alto, CA (US)

(72) Inventors: Richard N. Zare, Stanford, CA (US); Zhenpeng Zhou, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1271 days.

(21) Appl. No.: 15/843,876

(22) Filed: Dec. 15, 2017

(65) Prior Publication Data
US 2018/0173998 A1    Jun. 21, 2018

Related U.S. Application Data

(60) Provisional application No. 62/437,322, filed on Dec. 21, 2016.

(51) Int. Cl.
| | |
|---|---|
| *G06K 9/62* | (2022.01) |
| *G06N 20/00* | (2019.01) |
| *G06N 20/20* | (2019.01) |
| *G06N 20/10* | (2019.01) |
| *G06N 5/00* | (2006.01) |
| *G16H 50/20* | (2018.01) |
| *G16H 30/40* | (2018.01) |
| *G16H 50/30* | (2018.01) |

(52) U.S. Cl.
CPC ......... *G06K 9/6256* (2013.01); *G06K 9/6269* (2013.01); *G06K 9/6278* (2013.01); *G06K 9/6282* (2013.01); *G06N 5/003* (2013.01); *G06N 20/00* (2019.01); *G06N 20/10* (2019.01); *G06N 20/20* (2019.01); *G16H 30/40* (2018.01); *G16H 50/20* (2018.01); *G16H 50/30* (2018.01)

(58) Field of Classification Search
None
See application file for complete search history.

(56) References Cited

U.S. PATENT DOCUMENTS

| | | | |
|---|---|---|---|
| 7,923,682 | B2 | 4/2011 | Rowell et al. |
| 2006/0172429 | A1 | 8/2006 | Nilsson et al. |
| 2009/0261243 | A1 | 10/2009 | Bamberger et al. |
| 2014/0309121 | A1 | 10/2014 | Francese et al. |
| 2017/0329894 | A1* | 11/2017 | Kennedy ................. G16Z 99/00 |

OTHER PUBLICATIONS

"Mass Spectrometry-based Diagnostics: The Upcoming Revolution in Disease Detection" by Petricoin et al. (Year: 2003).*
(Continued)

*Primary Examiner* — Evren Seven
(74) *Attorney, Agent, or Firm* — Lumen Patent Firm

(57) ABSTRACT

Machine learning analysis of mass spectrometry spectra from human sweat samples is used to determine characteristics of interest such as age, ethnicity, gender drug use and disease state directly from the m/z data. This avoids the difficult problem of performing a full chemical analysis of human sweat samples to determine the characteristics of interest.

10 Claims, 11 Drawing Sheets

(56) References Cited

OTHER PUBLICATIONS

"Urine proteomics for profiling of human disease using high accuracy mass spectrometry" by Kentsis et al. (Year: 2009).*
"Automatic diagnosis of melanoma using machine learning methods on a spectroscopic system" by Li et al. (Year: 2014).*
Tang et al., "Chemical Imaging of Latent Fingerprints by Mass Spectrometry Based on Laser Activated Electron Tunneling", 2015, Anal. Chem. v87 pp. 2693-2701.
Huynh et al., "Forensic Identification of Gender from Fingerprints", 2015, Anal. Chem. v87 p. 11531-11536.
Brunelle et al., "New Horizons for Ninhydrin: Colorimetric Determination of Gender from Fingerprints", 2016, Anal. Chem. v88 pp. 2413-2420.
Bouslimani et al., "Lifestyle chemistries from phones for individual profiling", 2016, PNAS pp. E7645-E7654.

* cited by examiner

GROUP CLASSIFICATION BASED ON MACHINE LEARNING ANALYSIS OF MASS SPECTROMETRY DATA FROM SWEAT

CROSS REFERENCE TO RELATED APPLICATIONS

This application claims the benefit of U.S. provisional patent application 62/437,322, filed on Dec. 21, 2016, and hereby incorporated by reference in its entirety.

GOVERNMENT SPONSORSHIP

This invention was made with Government support under contract FA9550-16-1-0113 awarded by The Air Force Office of Scientific Research. The Government has certain rights in the invention.

FIELD OF THE INVENTION

This invention relates to analysis of human sweat specimens.

BACKGROUND

Fingerprint analysis is an important part of forensic science. Identification of individuals based on their fingerprint patterns has been known for many years. More recently, chemical analysis of fingerprints has been proposed to provide greater information from fingerprints, e.g., as described by Bouslimani et al. (PNAS, 14 Nov. 2016, pp. E7645-E7654). This work relates to the identification of specific molecules in fingerprint samples, and then correlating these molecules to lifestyles of the people the fingerprints are from.

However, identification of the presence/absence of specific molecules from trace samples such as fingerprints tends to be a difficult problem. Accordingly, it would be an advance in the art to provide analysis of fingerprints for characteristics of interest that did not require identification of specific chemical species.

SUMMARY

We have unexpectedly found that identification of chemical species in fingerprints is unnecessary for the larger goal of determining characteristics of interest from fingerprints or other sweat samples. These characteristics of interest can be age, gender, ethnicity and/or disease state. The main idea is to train a machine learning model on training data that has raw m/z mass spectrometry data associated with quantities of interest such as disease state etc. By training the model on such data, we have found that it ends up with the ability to determine characteristics of interest directly from the mass spectrometry m/z data, without any need for a difficult determination of which molecules are actually present in the samples. This is possible because of the large amount of data present in mass spectrometry m/z data. For example, it is commonplace for a single m/z spectrum to have over 500 peaks, each of varying relative height. No human could hope to see patterns in such complex data allowing the above-described classification to be performed, but we have found that this is possible with machine learning.

The description below provides a concrete example of this approach with respect to age, gender and ethnicity classification. This demonstration is important because there are several features of mass spectrometry m/z spectra that suggest such identification might not work in practice. The first such feature is that m/z spectra are in arbitrary units (i.e., only relative peak height information is available). There is no absolute height standard in such data. The second such feature of mass spectrometry m/z spectra is that chemical signatures in mass spectrometry are not unique. Any two ions having the same mass to charge ratio will end up contributing to the same m/z peak in a mass spectrometry spectrum. For this reason, separation techniques such as chromatography are often employed in connection with mass spectrometry. Demonstrating that such separation is unnecessary for the present application is a nontrivial contribution of the present work.

This approach can enable qualitatively new applications. These new applications include classification of an individual into different groups, such as gender, ethnicity, age, drug usage, and disease state, based on the chemical analysis of sweat, from various parts of the body, such as from fingerprints. Applications include forensic science and security. We also anticipate it can have wide-scale medical use. Significant advantages are provided. This approach is non-invasive, fast, inexpensive, and can be done with high accuracy.

DETAILED DESCRIPTION

Section A describes general principles relating to embodiments of the invention. Section B describes an experimental demonstration of principles of the invention. Section C provides further technical details for the example of Section B.

A) General Principles

Figure 1:
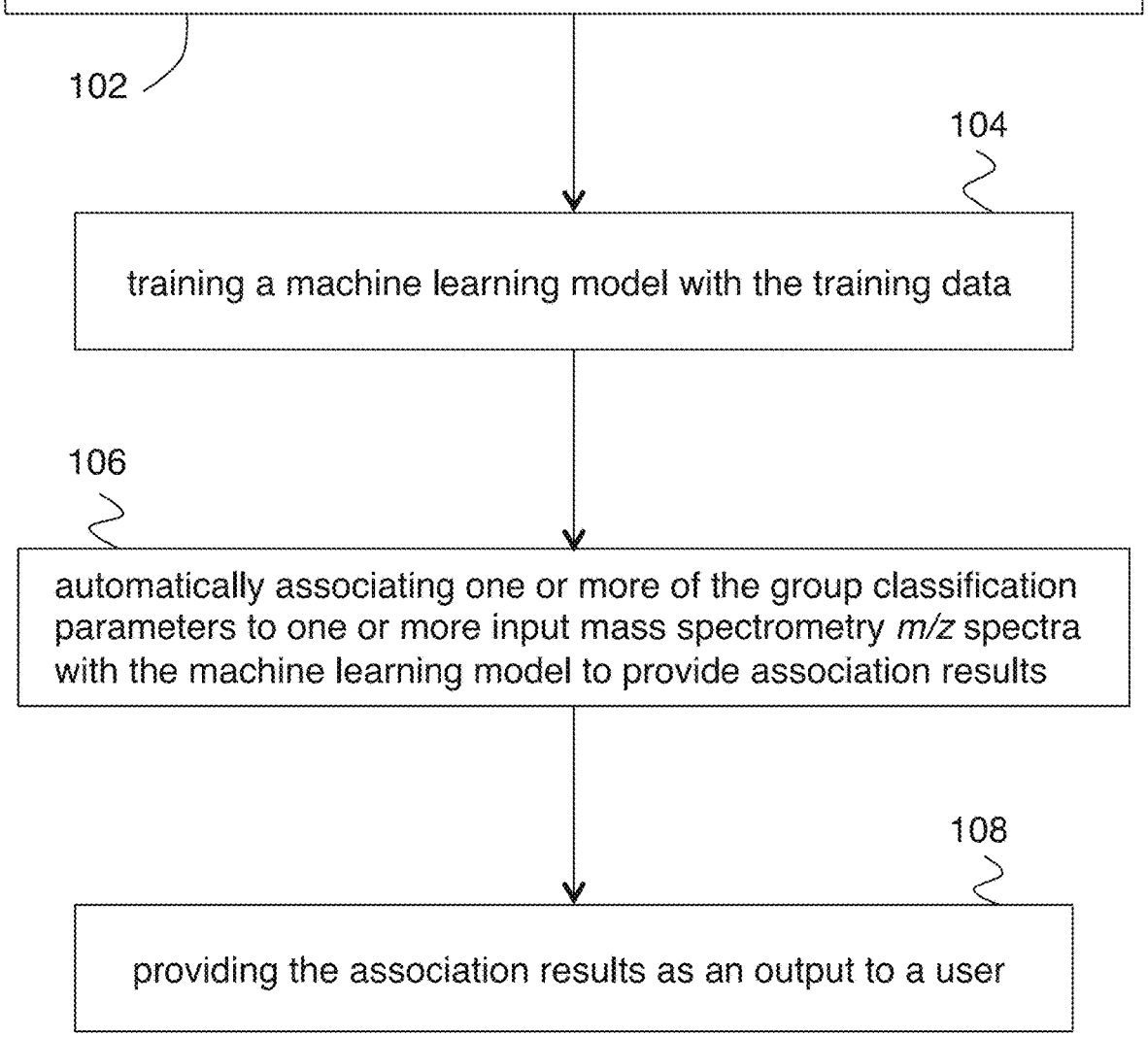
FIG. 1 is a flow chart for an embodiment of the invention.

FIG. 1 shows a method according to an embodiment of the invention. Overall, this is a method for providing classification of human sweat samples. Step 102 is providing a set of training data, where the training data includes 20 or more training mass spectrometry m/z spectra from training human sweat specimens, where each training mass spectrometry m/z spectrum is associated with one or more group classification parameters corresponding to the training human sweat specimens.

Step 104 is training a machine learning model on the set of training data.

Step 106 is automatically associating one or more of the group classification parameters to one or more input mass spectrometry m/z spectra from input human sweat specimens with the machine learning model to provide association results.

Step 108 is providing the association results as an output to a user.

The one or more group classification parameters can include but are not limited to: ethnicity, age ranges, gender, drug usage, and disease states. The disease states can include but are not limited to: diabetic disease states, cardiovascular disease states, kidney disease states, asthma disease states, cancer disease states, and cystic fibrosis disease states. The example of section B below relates specifically to ethnicity, age and gender, and can be regarded as proof of concept for detecting any disease state that affects sweat chemistry at least as much as ethnicity, age and gender do. It is expected that many significant medical conditions will have such altered sweat chemistry. For example, a recent study in our group found statistically significant relationships between the sweat profile change and dialysis disease state.

The machine learning model can be selected according to performance on a cross-validation data set including 20 or more cross-validation mass spectrometry m/z spectra from cross-validation human sweat specimens, where each mass spectrometry m/z spectrum is associated with one or more of the group classification parameters corresponding to the cross-validation human sweat specimens.

Suitable machine learning models include but are not limited to: logistic regression methods, support vector machines, random forests, gradient tree boosting methods, nearest neighbor methods, and Bayseian regression methods.

The input human sweat specimens can be from various sources such as: fingerprints, palm prints, forehead sweat and nose sweat. The input human sweat specimens are preferably obtained with a spatial resolution of 0.5 mm or less. Such spatial resolution can enable the association results to distinguish from each other two or more overlapping input human sweat specimens from different people (e.g., from overlapping fingerprints).

Mass spectrometry m/z spectra for this approach are preferably raw m/z spectra where no separation (e.g., chromatography etc.) of the sweat sample is performed prior to the mass spectrometry.

B) Experimental Demonstration
B1) Introduction

Fingerprints are important in forensic sciences for identification of criminals. Most of the fingerprint analysis methods focus on visual comparison and imaging. However, fingerprints, whose composition are mostly sweat, possess the potential to provide more personal information. It is known that the composition of fingerprints, which consists primarily of lipids, sterols, and amino acids, differs between individuals. On the other hand, metabolism is affected by several factors including age, gender, and inheritance. Sweat, which is the main excretion found in fingerprints, is closely related to human metabolism. Therefore, it is expected that its chemical analysis might offer personal information such as gender, age, ethnicity, medical history and drug usage.

A number of computer vision techniques have been used to characterize the personal information from fingerprints, by looking at the patterns of the fingerprint images. Sex, ancestral, and pattern type variation in fingerprint minutiae have been studied. Fingerprints have been classified based on deep neural networks. A hybrid system has been considered using faces and fingerprints for user recognition. These methods, however, require the fingerprint images to be clear and with high resolution, which is challenging in many real applications.

Mass spectrometry or spectroscopic techniques have been used to characterize the endogenous composition of fingerprints. Desorption electrospray ionization mass spectrometry imaging (DESI-MSI) has been demonstrated for fingerprint imaging and explosives detection. Spectroscopic and chemical imaging of latent fingerprints has also been demonstrated. Colorimetric methods have been considered for gender detection. However, these methods do not make full use of the huge amount of chemical information that the instrument makes available.

In this work, ambient ionization mass spectrometry and machine learning were coupled to analyze latent fingerprints, utilizing the ability of machine learning methods to dig through the enormous chemical information that mass spectrometry provides. In addition, by feature selection of the machine learning model and tandem mass spectrometry, the specific molecules that are different between individuals could be pinpointed.

B2) Materials and Methods
B2.1) Human Subject Approval

The research was approved by Stanford Research Compliance Office, Human Subjects Research Institutional Review Board (IRB). The protocols were carried out in accordance with IRB regulations.

B2.2) Fingerprint Collection

Hands were washed by soap and dried in air, before being placed into polyethylene (PE) gloves for 60 min to accelerate perspiration. Fingerprint imaging samples were produced by pushing fingers onto a glass slide for 1 s.

B2.3) Lipid Sample Collection

Lipid samples from fingerprints were collected by the procedure described above. Lipid samples from forehead were collected by swiping a glass slide on the forehead of a consenting adult.

B2.4) Mass Spectrometry Imaging

Desorption electrospray Ionization (DESI) was set up for fingerprint imaging and lipid sample analysis. A custom-built DESI source with an x-y stage coupled to an LTQ-Orbitrap XL mass spectrometer (Thermo Scientific) was used. The spectrum was collected under negative ion mode with m/z 150 - 1000. The DESI source used methanol:water (9:1 v/v) as the solvent with a flow rate of 1 µL/min. The nitrogen gas pressure was set to 80 psi. The spatial resolution of the imaging was estimated to be 200 µm.

B2.5) Data Analysis

The Xcalibur raw files were read and converted to Python files. A peak finding algorithm was applied to convert the continuous spectrum to sparse peak data. 1634 peaks were found in each sample. Data purge, including discarding samples with too few peaks or low peak intensities, was applied to the data set. Each sample was then vectorized by the peak values with a resolution of 0.1 m/z. Samples were normalized by L1 norms of the sample vectors, which is dividing the sample vector by the sum of absolute values in the vector. Algorithms were adapted from open source software tools xgboost and scikit-learn. The samples were separated into a training set, a cross-validation set, and a test set, with ratio of 7:1.5:1.5.

Classification algorithms of logistic regression, support vector machines, random forests, gradient tree boosting, nearest neighbors, and Bayesian regression were tested. Model selection was based on the performance of the cross-validation set.

B3) Result and Discussion

B3.1) Different Source of Lipids

Figure 2:
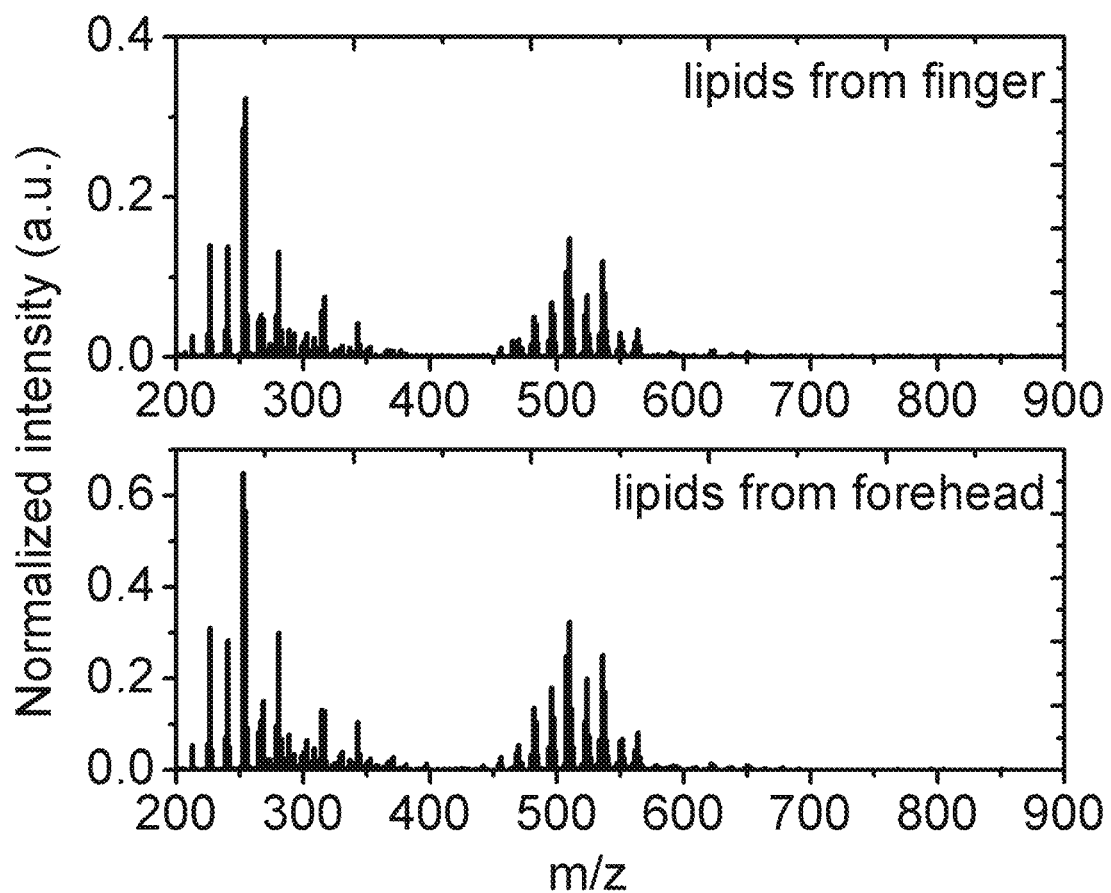
FIG. 2 shows a comparison of mass spectrometry data from a fingerprint sweat sample and a forehead sweat sample.

Lipids from forehead and fingerprints were taken from 8 people and analyzed by mass spectrometry. The spectra of lipids from forehead and finger are shown on FIG. 2 and show no significant differences under statistical t-test with 95% confidence interval, showing different sources of lipids from the same people have similar composition. It can be inferred from these results that the secretory glands from fingers and forehead are similar in products. This figure demonstrates that sweat from any part of the body is the same, which greatly simplifies the task of sweat collection.

B3.2) Mass Spectrometry Imaging of Fingerprints

Figure 3:
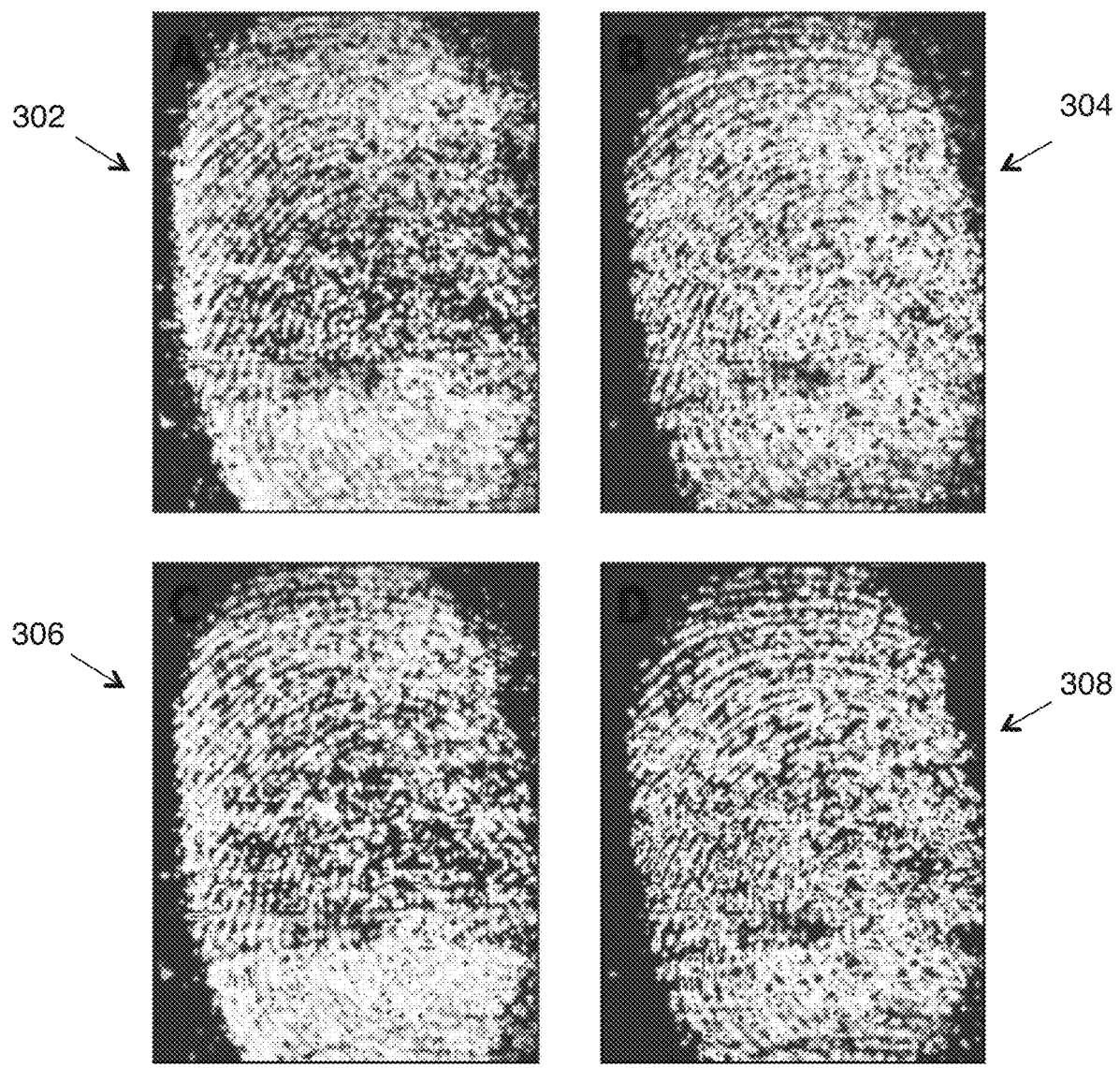
FIG. 3 shows exemplary spatial fingerprint patterns at several mass spectrometry m/z peaks.
Figure 4A:
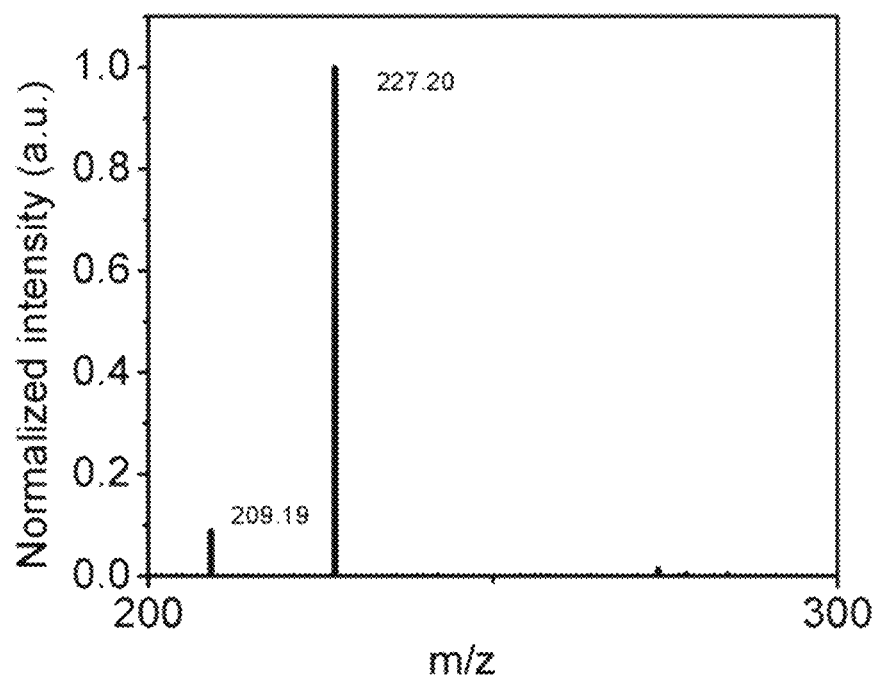
FIGS. 4A-D show tandem mass spectrometry spectra relating to the data of FIG. 3.
Figure 4B:
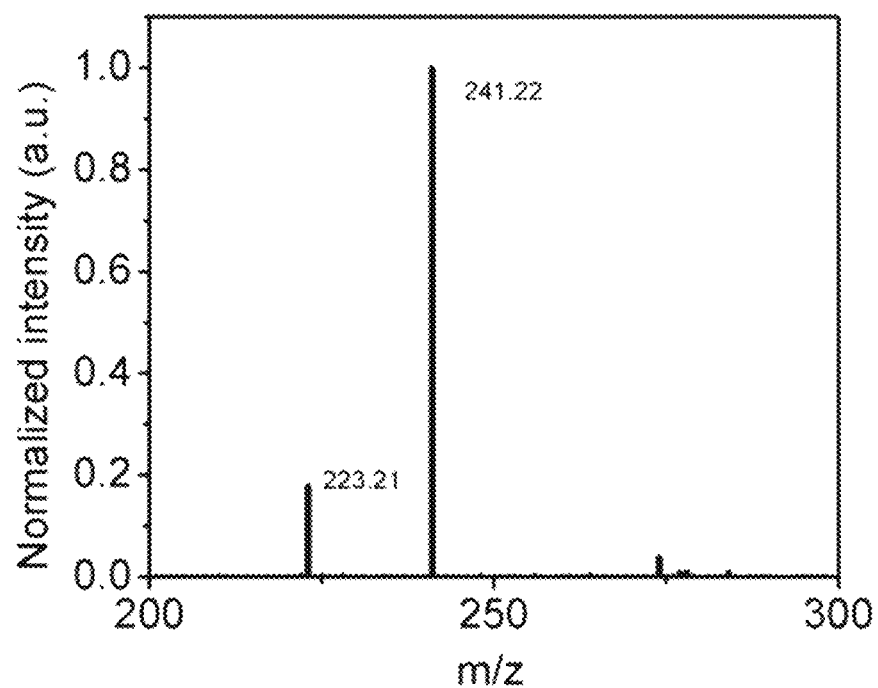
Figure 4C:
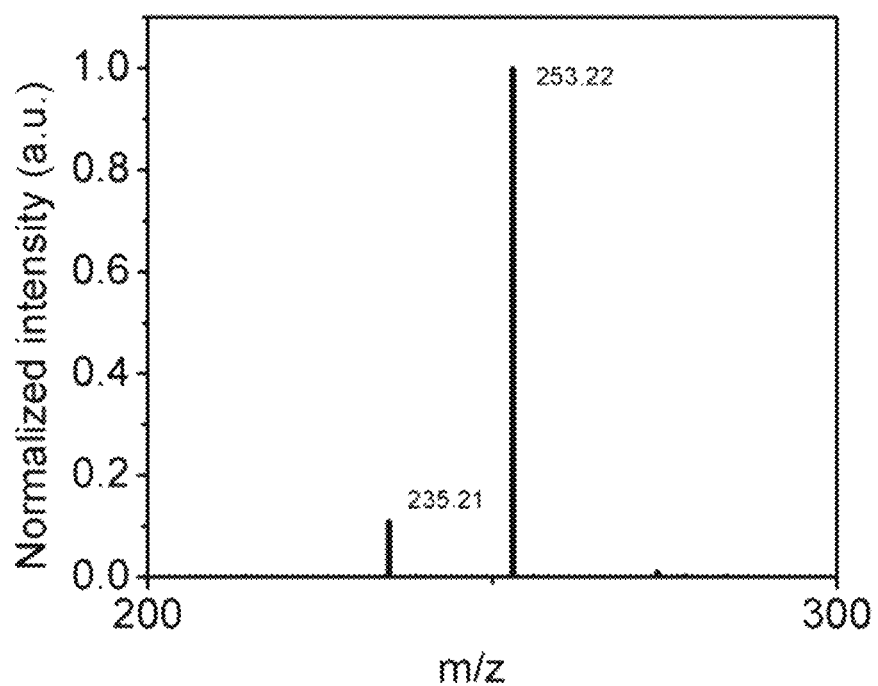
Figure 4D:
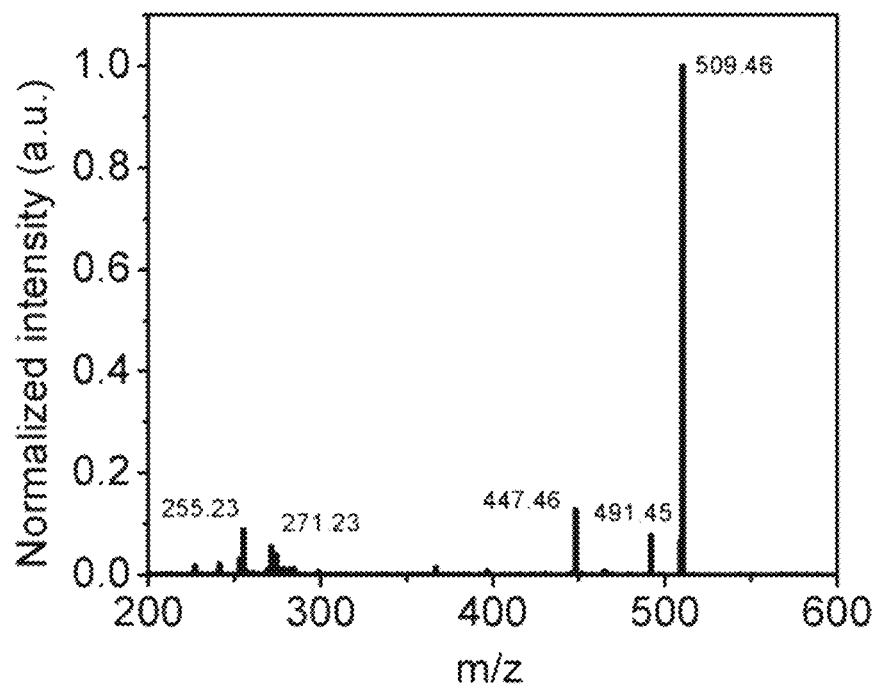

FIG. 3 shows selected negative ion mode DESI imaging of the same fingerprint at m/z 227, m/z 241, m/z 253, and m/z 509, referenced as 302, 304, 306, and 308 respectively. Most of the species show spatial homogeneity, indicating that the secretory products are nearly the same throughout the image. On the other hand, the spatial fingerprint pattern can be detected from the mass spectrometry imaging of the fingerprint. Tandem mass spectrometry data shows that the four peaks can be identified as (m/z 227) FA(14:0), (m/z 241) FA(15:0), (m/z 253) FA(16:1), and (m/z 509) DG(16:0|12:1(OH)). Abbreviations: FA is short for fatty acid, FA(14:0) represents all chain permutations of fatty acids with 14 carbons and 0 double bonds. DG is short for di(acyllalkyl)glycerols, DG(16:0|12:1(OH)) represents all chain permutations of diacylglycerols, whose acyl chains are fatty acyls with 16 carbons and 0 double bonds, and are fatty acyls of 12 carbons with 1 double bond, and 1 OH substitution. FIGS. 4A-D shows the tandem mass spectra of m/z=227.20 (FIG. 4A), m/z=241.22 (FIG. 4B), m/z=253.22 (FIG. 4C), and m/z=509.46 (FIG. 4D).

B3.3) Classification by Machine Learning Models

By swiping a glass slide across the forehead of a consenting adult, samples with similar lipid compositions as fingerprints were obtained, yielding a sample size of 203. A machine learning algorithm of gradient boosting tree ensemble (GDBT) was applied on the samples to classify them between different genders, ethnicities (American, Chinese, European, and Indian), and ages (20, 30, 40-50, 60 and above). A discriminative model was trained on the training set, and the hyper-parameters were optimized on the cross-validation set. The final classification accuracy was 89.2%, 82.4%, and 84.3% respectively on test sets, showing we can determine with good accuracy the gender, ethnicity, and age of a person from the lipid profile.

Figure 5:
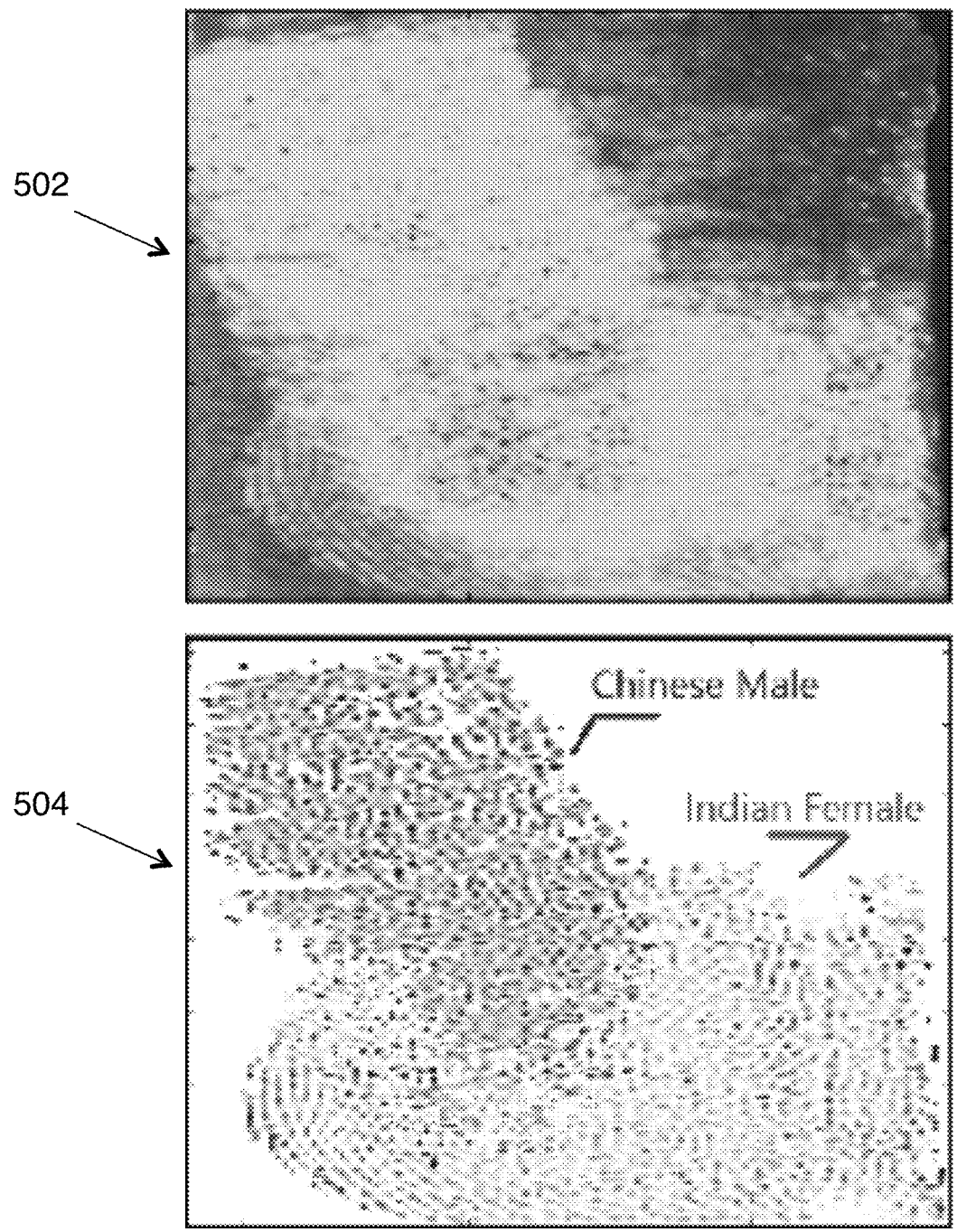
FIG. 5 shows classification used to distinguish overlapping fingerprints from different people.

Two overlaid fingerprints from different people was imaged by DESI-MSI, as an illustration of the classification model. Lower resolution than previous was used to protect the privacy of individuals who provided their fingerprints. Image 502 on FIG. 5 shows the negative ion mode DESI-MS ion images of m/z 253, from which the two fingerprints are recognizable, although the boundary is not clear enough, as fingerprints have similar compositions. Image 504 on FIG. 5 shows the classification results for each pixel in image 502 from the pretrained model. The pixels which are predicted to belong to a Chinese male are shown in dark grey, while the pixels which are predicted to be from an Indian female are shown in light gray. In both cases, the predictions were correct. The discriminative model is able to get personal information from the fingerprints, resulting in a better separation of the fingerprints.

B3.4) Feature Selection and Identification

Figure 6A:
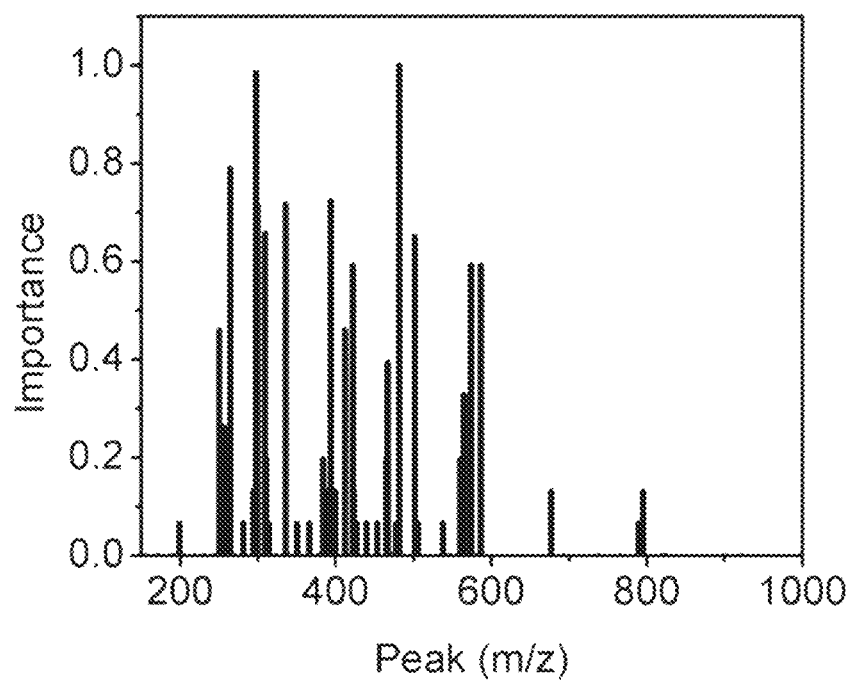
FIG. 6A shows relative importance of various m/z peaks for gender classification.
Figure 6B:
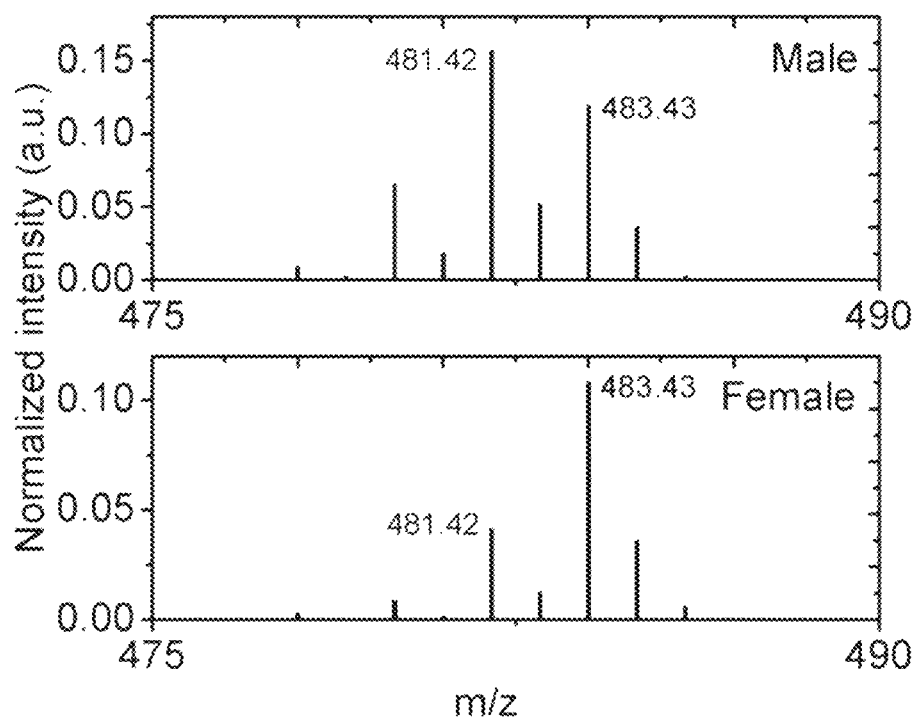
FIG. 6B shows tandem mass spectrometry spectra relating to the data of FIG. 6A.

The peak finding algorithm found 1634 peaks in the samples, indicating 1634 molecular features that can provide useful information, which makes data interpretation difficult. On the other hand, we need to know the molecular differences in lipid profiles between different groups of people. The GDBT model is capable of feature selection by finding features that maximize the decreases of weighted impurity in a tree. By ranking the features with their decreases of impurity in the model that yielded the lowest test errors, the relative feature importance in gender classification is shown in FIG. 6A. FIG. 6B shows the sample spectrum of male and female, zoomed at peak of m/z=481.42, which is determined to be important by the feature selection algorithm.

Figure 7A:
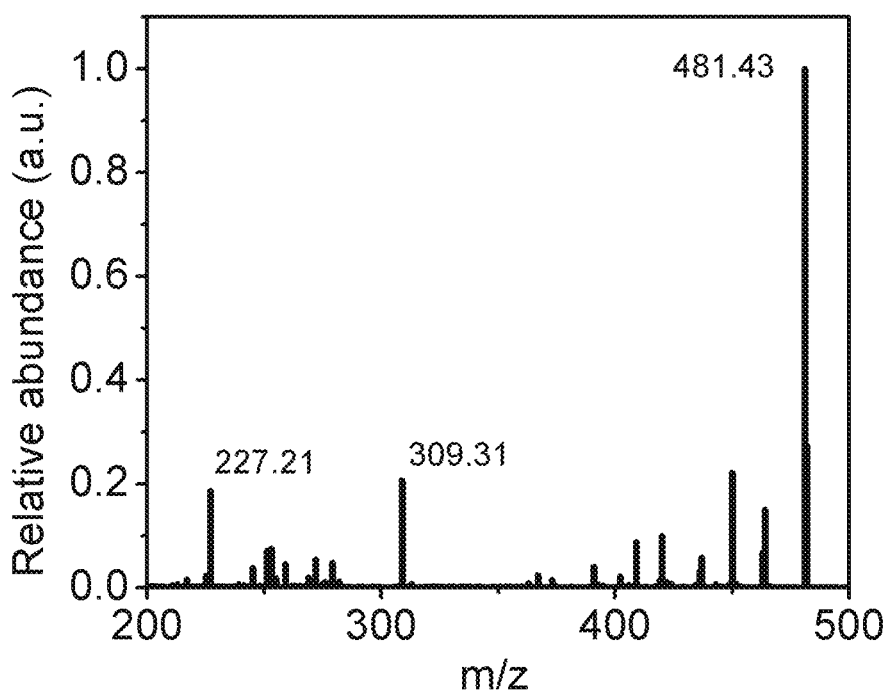
FIGS. 7A-B show mass spectrometry m/z peaks relating to gender and ethnicity classification.
Figure 7B:
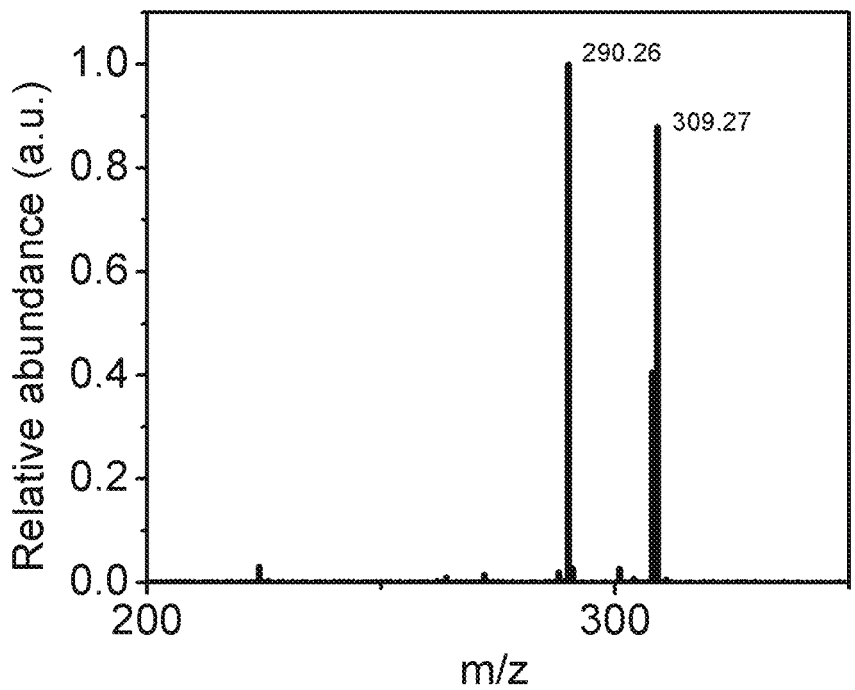
Figure 8:
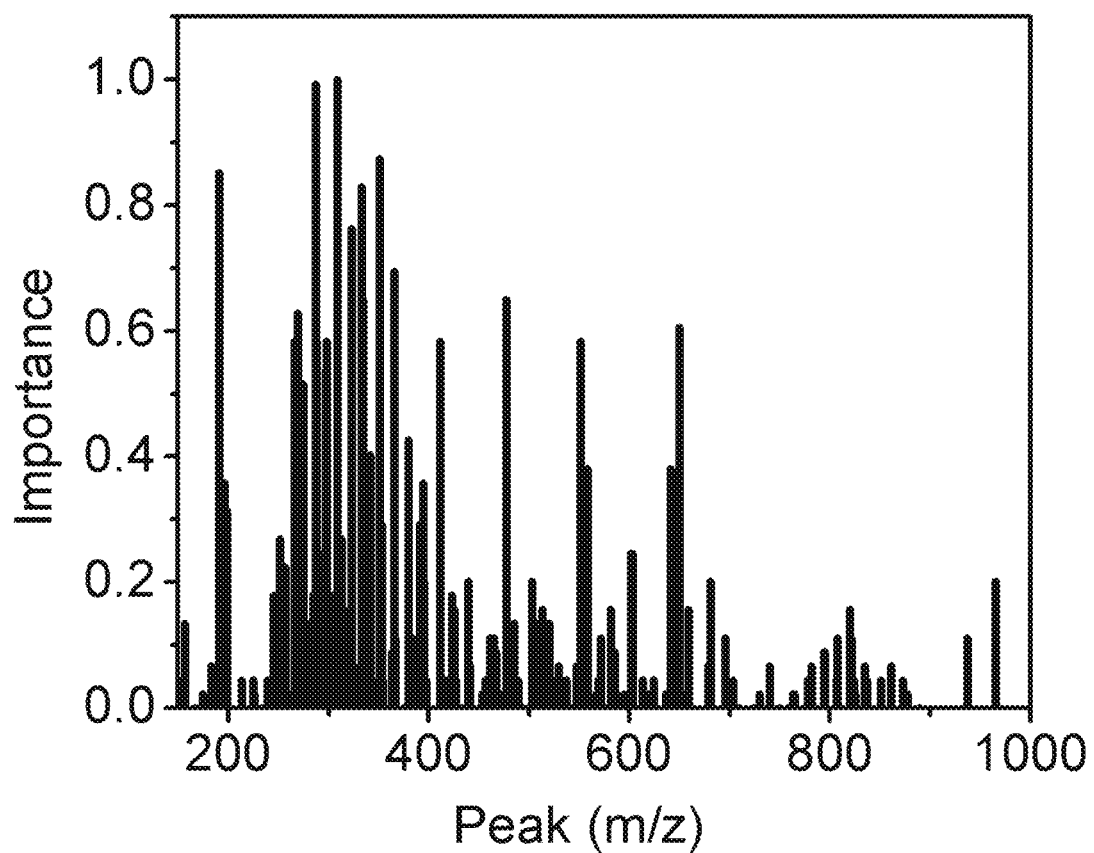
FIG. 8 shows relative importance of various m/z peaks for ethnicity classification.
Figure 9:
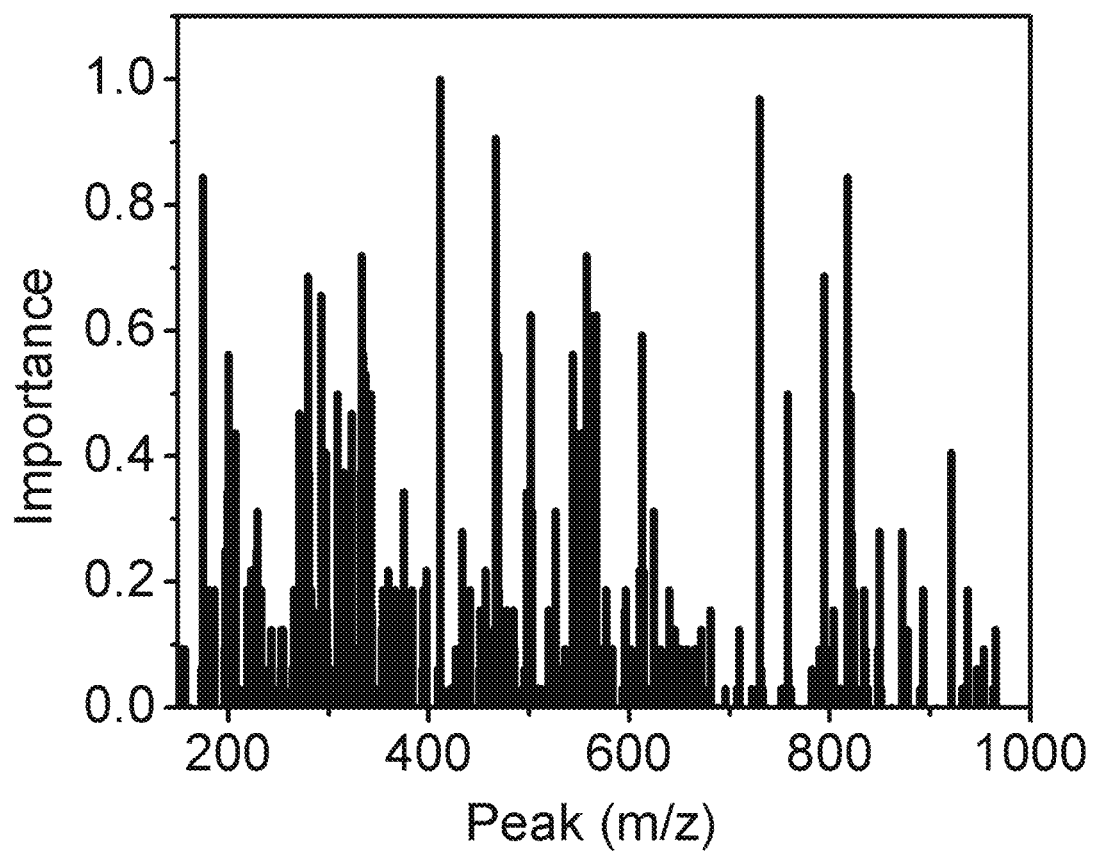
FIG. 9 shows relative importance of various m/z peaks for age classification.
Figure 10:
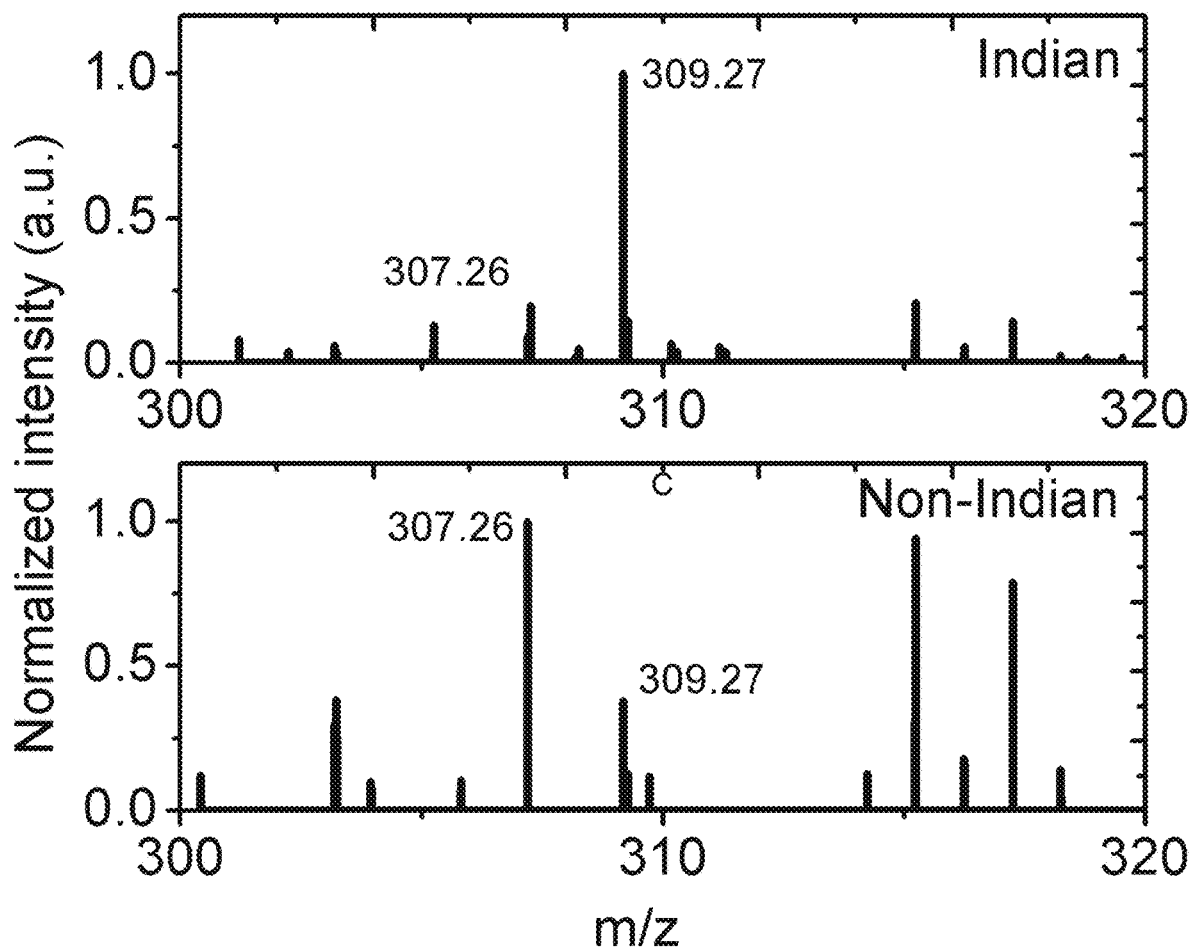
FIG. 10 shows tandem mass spectrometry spectra relating to the data of FIG. 8.

Many peaks selected as important features by the model were then tentatively identified by tandem mass spectrometry with high mass resolution and accuracy. For example, the species with m/z=481.42534 was selected as an important feature in gender classification (with relative importance of 0.93), was then identified as DG(16:1|10:0) in the tandem mass spectrometry results shown on FIG. 7A. Similarly, FIG. 7B shows tandem mass spectra of (A) m/z=309.27, which is important in ethnicity classification. FIGS. 8 and 9 show the features selected in the GDBT analysis to be important in the classification of ethnicity and age, respectively, as determined by tandem mass spectra of some important peaks in FIG. 7A. The sample spectra of different ethnicities are shown in FIG. 10, showing the peak at m/z=309.27 which is determined to be important with feature selection algorithm. Although the chemical information of the features is not necessary for classification, the feature selection and identification results illustrate that the method is capable of locating important molecules that can uncover human metabolism variance between different groups.

B4) Conclusion

In this work, mass spectrometry imaging was performed on fingerprints, for which pattern and chemical information can be obtained at the same time. Personal information of gender, ethnicity, and age can be obtained by applying a classification algorithm of gradient boosting tree ensemble on the lipid profiles on 203 samples, with accuracies of 89.2%, 82.4%, and 84.3%, respectively. The pretrained model was applied on two overlaid fingerprints, showing the capability of obtaining personal information, and achieving better separation. In addition, by feature selection using the GDBT machine learning model, the species that are significant for classification between different groups of people were able to be found, and then their chemical composition identified by tandem mass spectrometry. This information provides new chemistry-biology insights of human metabolism. Finally, this work provides evidence that the mass spectrometry combined with machine learning can be a valuable tool for determining personal information by a noninvasive method.

C) A Brief Introduction to Gradient Boosting Tree

C1) Model and Parameters

The model in supervised learning usually refers to the mathematical structure of how to make the prediction $y_i$ given $x_i$. For example, a common model is a linear model, where the prediction is given by $y_i = \Sigma_j \theta_j x_{ij}$, a linear combination of weighted input features.

The parameters are the undetermined part that we need to learn from the data. In linear regression problems, the parameters are the coefficients $\theta$. Usually we will use $\theta$ to denote the parameters.

C2) Objective Function: Training Loss+Regularization

The objective function is defined to measure the performance of the model given a certain set of parameters. It usually contains two parts: training loss and regularization.

$$Obj(\theta) = L(\theta) + \Omega(\theta)$$

where L is the training loss function, and $\Omega$ is the regularization term. The training loss measures how predictive our model is on training data. The regularization term controls the complexity of the model, which helps us to avoid overfitting.

C3) Additive Training

Gradient boosting combines weak learners into a single strong learner, in an iterative way. We use an additive strategy: fix what we have learned, add one new model at a time. We note the prediction value at step t by $\hat{y}_i^{(t)}$, so we have $$\hat{y}_i^{(0)} = 0$$

$$\hat{y}_i^{(t)} = \sum_{k=1}^{t} f_k(x_i) \hat{y}_i^{(t-1)} + f_t(x_i)$$

Then the objective function is given by $$obj^{(t)} = \sum_{i=1}^{n} l(y_i, \hat{y}_i^{(t)}) + \sum_{i=1}^{t} \Omega(f_i) = \sum_{i=1}^{n} l(y_i, \hat{y}_i^{(t-1)} + f_t(x_i)) + \sum_{i=1}^{t} \Omega(f_i)$$

C4) The Tree Structure

Refine the definition of a tree f(x) as:

$$f_t(x) = w_{q(x)}, \; w \in \mathbb{R}^T, \; q: \mathbb{R}^d \rightarrow \{1, 2, \ldots, T\}$$

Here w is the vector of scores on leaves, q is a function assigning each data point to the corresponding leaf and T is the number of leaves in the tree.

Then the objective value, with second-order Taylor expansion, is:

$$obj^{(t)} = \sum_{i=1}^{n} \left( g_i w_{q(x_i)} + \frac{1}{2} h_i w_q(x_i)^2 \right) + \gamma T + \frac{1}{2} \lambda \sum_{i=1}^{T} w_j^2$$

where $g_i$ and $h_i$ are defined as $$g_i = \partial_{\hat{y}_I^{(t-1)}} l(y_i, \hat{y}_I^{(t-1)})$$

$$h_i = \partial_{\hat{y}_I^{(t-1)}}^2 l(y_i, \hat{y}_I^{(t-1)})$$

C5) Learn the Tree Structure

We can compress the expression by defining $I_j = \{i | q(x_i) = j\}$, $G_j = \sum_{i \in I_j} g_i$, and $H_j = \sum_{i \in I_j} h_i$:

$$obj^{(t)} = \sum_{j=1}^{T} \left( G_j w_j + \frac{1}{2}(H_j + \lambda) w_j^2 \right) + \gamma T$$

The best objective reduction we can get is:

$$obj^* = -\frac{1}{2} \sum_{j=1}^{T} \frac{G_j^2}{H_j + \lambda} + \gamma T$$

The score it gains when we try to split a leaf into two leaves is:

$$Gain = \frac{1}{2}\left( \frac{G_L^2}{H_L + \lambda} + \frac{G_R^2}{H_R + \lambda} - \frac{(G_L + G_R)^2}{H_L + H_R + \lambda} \right) - \gamma$$

This formula can be decomposed as 1) the score on the new left leaf, 2) the score on the new right leaf, 3) the score on the original leaf, and 4) regularization on the additional leaf. The Gain can be used in feature selection.

The invention claimed is:

1. A method for providing classification of human sweat samples, the method comprising:
   providing a set of training data, wherein the training data includes 20 or more training mass spectrometry m/z spectra from training human sweat specimens, wherein each training mass spectrometry m/z spectrum is associated with one or more group classification parameters corresponding to the training human sweat specimens;
   training a machine learning model on the set of training data;
   automatically associating one or more of the group classification parameters to one or more input mass spectrometry m/z spectra from input human sweat specimens with the machine learning model to provide association results;
   providing the association results as an output to a user.

2. The method of claim 1, wherein the one or more group classification parameters are selected from the group consisting of: ethnicity, age ranges, gender, drug usage, and disease states.

3. The method of claim 2, wherein the disease states are selected from the group consisting of: diabetic disease states, cardiovascular disease states, kidney disease states, asthma disease states, cancer disease states, and cystic fibrosis disease states.

4. The method of claim 1, further comprising selecting the machine learning model according to performance on a cross-validation data set including 20 or more cross-validation mass spectrometry m/z spectra from cross-validation human sweat specimens, wherein each mass spectrometry m/z spectrum is associated with one or more of the group classification parameters corresponding to the cross-validation human sweat specimens.

5. The method of claim 4, wherein the machine learning model is selected from the group consisting of: logistic regression methods, support vector machines, random forests, gradient tree boosting methods, nearest neighbor methods, and Bayeseian regression methods.

6. The method of claim 1, wherein the input human sweat specimens are from one or more sources selected from the group consisting of: fingerprints, palm prints, forehead sweat and nose sweat.

7. The method of claim 6, wherein the input human sweat specimens are obtained with a spatial resolution of 0.5 mm or less.

8. The method of claim 7, wherein the association results are used to distinguish from each other two or more overlapping input human sweat specimens from different people.

9. The method of claim 1, wherein the training mass spectrometry m/z spectra are raw spectra from the training human sweat specimens with no chemical separation employed.

10. The method of claim 1, wherein the input mass spectrometry m/z spectra are raw spectra from the input human sweat specimens with no chemical separation employed.

\* \* \* \* \*